United States Patent
Zhang et al.

(10) Patent No.: US 9,024,781 B2
(45) Date of Patent: *May 5, 2015

(54) CARDIAC ELECTRICITY AND IMPEDANCE MONITORING MOBILE NETWORK TERMINAL DEVICE HAVING FUNCTION OF MICRO CURRENT RELEASE

(71) Applicant: Jinjing Zhang, Jinan (CN)

(72) Inventors: Jinjing Zhang, Jinan (CN); Yonggang Zhao, Jinan (CN); Haiqing Gao, Jinan (CN); Yungdai Chen, Jinan (CN); Yujie Zhou, Jinan (CN); Shaowen Liu, Jinan (CN); Xiaohong Zhu, Jinan (CN)

(73) Assignee: Jinjing Zhang, Jinan, Shandong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,252

(22) Filed: Jun. 27, 2014

(65) Prior Publication Data

US 2014/0320309 A1 Oct. 30, 2014

Related U.S. Application Data

(63) Continuation-in-part of application No. 12/998,809, filed on Jul. 14, 2011, now Pat. No. 8,836,535.

(51) Int. Cl.
*G08C 19/22* (2006.01)
*H04Q 9/00* (2006.01)
(Continued)

(52) U.S. Cl.
CPC ............ *H04Q 9/00* (2013.01); *H04Q 2209/823* (2013.01); *A61B 5/7455* (2013.01); *A61B 5/746* (2013.01); *A61B 5/747* (2013.01);
(Continued)

(58) Field of Classification Search
CPC .......... H04M 1/72536; H04M 1/2535; H04M 2250/12; A61B 5/0013; A61B 5/7232; A61B 5/01; A61B 5/0404; A61B 5/0809; A61B 5/7455; A61B 5/4818; A61B 5/0002; A61B 5/746; A61B 5/747; A61B 5/1112; A61B 5/1116; A61B 5/14542; H04Q 9/00; H04Q 2209/823; G06F 19/34; A61M 2021/0072; A61M 2021/0083; A61M 21/00
USPC ............... 340/870.07, 573.1, 286.07, 539.12, 340/870.09, 573.4, 539.1, 539.11, 3.1, 340/5.61; 379/38, 37; 455/404.1, 404.2; 607/60; 600/300, 301, 481

See application file for complete search history.

(56) References Cited

U.S. PATENT DOCUMENTS

| 6,057,758 A * | 5/2000 | Dempsey et al. ........ 340/539.12 |
| 8,836,535 B2 * | 9/2014 | Zhang et al. ............. 340/870.07 |
| 2003/0107487 A1* | 6/2003 | Korman et al. ............ 340/573.1 |

*Primary Examiner* — Anh V La
(74) *Attorney, Agent, or Firm* — CBM Patent Consulting, LLC

(57) ABSTRACT

A cardiac electricity and impedance monitoring mobile network terminal device having function of micro current release is provided which includes a baseband processor module, an electrophysiological data collection module, a micro current stimulator module, a keyboard module, a graphics and image display module, an image and picture sensor, a voice communication module, an external data memory card, an external data memory, a short distance digital communication module, a USB interface module, a GPS receiver module, an application module set and run in the operation system of the baseband processor; a cardiac electricity and breast impedance data remote monitoring, a sleep snore data monitoring, a pathological image remote monitoring, a short distance data/information exchange, a medical advisory VoIP voice communication and a network emergency recourse being implemented by the mobile network terminal device under the control of the application program module.

19 Claims, 5 Drawing Sheets

(51) Int. Cl.
  *A61B 5/00* (2006.01)
  *G06F 19/00* (2011.01)
  *A61B 5/01* (2006.01)
  *A61B 5/0404* (2006.01)
  *A61B 5/08* (2006.01)
  *A61B 5/11* (2006.01)
  *A61B 5/145* (2006.01)
  *A61M 21/00* (2006.01)

(52) U.S. Cl.
  CPC ............... *A61B 5/0002* (2013.01); *A61B 5/01* (2013.01); *A61B 5/0404* (2013.01); *A61B 5/0809* (2013.01); *A61B 5/1112* (2013.01); *A61B 5/1116* (2013.01); *A61B 5/14542* (2013.01); *A61B 5/4818* (2013.01); *A61M 21/00* (2013.01); *G06F 19/34* (2013.01); *A61M 2021/0072* (2013.01); *A61M 2021/0083* (2013.01)

CARDIAC ELECTRICITY AND IMPEDANCE MONITORING MOBILE NETWORK TERMINAL DEVICE HAVING FUNCTION OF MICRO CURRENT RELEASE

This application is a continuation-in-part application of U.S. application Ser. No. 12/998,809 filed 14 Jul. 2011 which is a continuation of is the U.S. national phase of International Application No. PCT/CN2009/000421 Filed 21 Apr. 2009 which designated the U.S. and claims priority to Chinese Application No. 200810239037.4 filed 5 Dec. 2008, the entire contents of each of which are hereby incorporated by reference.

TECHNICAL FIELD OF THE INVENTION

The present invention relates to remote monitoring of a heart and breath status of a patient in sleep, more particularly, to a mobile network terminal device for monitoring cardiac electrophysiological data and breast impedance data and capable of releasing micro current.

BACKGROUND OF THE INVENTION

A sleep apnea syndrome is a high incidence disease over the world. In China, the prevalence rate reaches 4% in the adult, and the number is up to 30,000,000. It is a kind of disease with a high prevalence rate and disserving health of human beings seriously. A sudden death occurred in sleep is associated closely with a breath sudden-break. The breath of human beings is a complicated procedure in which the activity of muscle and nerve in the respiratory tract plays a critical role in maintaining the breath of human beings, guarantees the openness and aeration of the airway. In sleep, the parasympathetic nerves are excited, the muscles of the respiratory tract are relaxed, and the airway is collapsed and narrowed; when awaking, the sympathetic nerves are excited, the tension of the muscles of the respiratory tract is strengthened, and the caliber of the airway is enlarged. Most of sleep apnea syndrome are caused by the sleep posture, which incurs the more serious collapse or even choke of the respiratory tract. Although the respiratory muscles (the diaphragm, and the abdominal muscles, etc.) work hard, the airway is narrow and choked, the sudden-break of breath occurs, acute snore appears, the blood oxygen saturation decreases, the cardiac electrophysiology is in disorder, and even the heart sudden death occurs in sleep. If the patient adjusts the sleep posture or is aroused from sleep, the respiratory tract may be reopened, and the respiratory function is recovered immediately. The status where the oxygen is insufficient is improved, the snore is stopped, and the cardiac emergency incurred by hypoxia can be avoided.

An existing method for diagnosing the sleep apnea syndrome is that the patient lives in a sleep lab in a hospital; a PSG, a POM, a PEFR, an EOG and so on are used to monitor the EEG, the blood oxygen saturation, the peak of a breath airflow, the variation of the retina voltage of the eyes; and a clinic diagnosis is performed. Nevertheless, it is a heavy burden for both of the medical resource in the hospitals and the social medical insurance that such conspicuous amount of patients in the society are examined by hospitalization, and the cost is high. Meanwhile, the operation is complex, and the cost per examination is expensive. The patient is required to wear 4-6 instruments during the examination, feels hard to fall in sleep, generates antagonistic psychology even, and refuses the examination.

Afterwards, a monitor system for the sleep apnea syndrome used in home is present, and the patient is not necessary to make a queue to wait for the examination by living in the hospital, and the diagnosis for the sleep apnea syndrome could be made at home. Eden Trace system uses a breast impedance monitor, a breath airflow monitor and a blood oxygen saturation monitor to monitor and examine the sleep apnea syndrome for the patient, and the result is highly consistent with the examining result of the sleep lab in the hospital. Night Watch system uses five devices including an eye-movement graph, the blood oxygen saturation monitor, the breath airflow monitor and so on to monitor the sleep apnea syndrome for the patient at home. The monitor record may be sent to the computer in the hospital through the public telecommunication network with a Modem connected therewith, and the doctor may observe the connection status of the devices mounted on the patient for 24 hours, and evaluates the signal quality. A MESAM system uses a sleep snore monitor and the blood oxygen saturation monitor to monitor the sleep apnea syndrome for the patient at home. U.S. Pat. No. 7,258,670B2 discloses that a breath monitor device is managed by a personal computer, the recorded sleep apnea data can be sent via a network to a server in the hospital for a comparison and analysis with the sleep breath data sample in a database. Recently, a home sleep apnea monitor technology utilizing a digital mobile phone transmission is available, and the data is transmitted to the server in the hospital after finishing the monitor so as to make an analysis, diagnosis and treatment.

Some of those existing home sleep apnea monitor technologies are complex in device structures, in which the patient is required to wear 3-4 instruments, inconvenient for use, and hard to be accepted by for the patient; some of them require the doctor to observe remotely for 24 hours, the number of the served patients is limited, and the medical cost is expensive; some of them are too simple in structures, the collected data is simple, and the doctor cannot determine the cardiac complications conditions of the patient from the data. Those existing technologies do not have a function for analyzing and intervening in real-time, and they rely on the process in which the data is uploaded and transmitted to the sever in the hospital after finishing the monitor, or a data storage device is delivered to the hospital for analyzing and processing. It takes a long time for the patient to obtain the doctor's advices. Actually, even if the doctor knows the patient at home is encountering a serious sleep apnea, or the sleep apnea is incurring a disordered cardiac electrophysiology, a real time intervening cannot be made, which is very dangerous for the patient. It is needed in the market a simple sleep apnea monitor device which may provide a real-time analysis and diagnosis. When the patient is found in a high-risk status, a quick intervening can be made so as to prevent the disease from deteriorating and lower the patient's risk.

SUMMARY OF THE INVENTION

The object of the present invention is to address the existing problem in the home sleep apnea monitor technology, and provide a simply used mobile network terminal device for a synchronous monitor of the cardiac electricity and the breast impedance, such that the critical data, such as breath, cardiac electricity, snore, blood oxygen saturation, and posture, is obtained to be analyzed and screened in real-time. When the patient is found in a high-risk status, a real-time intervening can be made so as to facilitate the recovery of the breath function of the patient and cancel the factors incurring the disordered cardiac electrophysiology.

The present invention provides a mobile network terminal device for monitoring cardiac electricity and breath data and capable of releasing a micro current, characterized in that, comprises a baseband processor module, an electrophysiological data collection module, a keyboard module, a graphic and image display module, an image and picture sensor, a voice communication module, a data storage card, a data memory, a short distance digital communication module, a USB interface module, a GPS receiver module, an application program module set and executed in an operation system of the baseband processor module, and an external micro current stimulator module. The operation system is embedded with a TCP/IP protocol, a short distance digital communication protocol, a USB protocol, a WAP browser, an instant communication protocol, a VoIP protocol, a multimedia software, and a primary language text font. The short distance digital communication circuit is in a dual-mode standard, supports 802.11x and Bluetooth protocols. Bluetooth is used to connect the mobile network terminal device to the external micro current stimulator module wirelessly, and Wi-Fi is used to connect the mobile network terminal device to the external Wi-Fi network device wirelessly, under the control of the application program.

The principle of the present invention is that the mobile network terminal device controls the user's information data, the function status, and work mode through the application program module, accesses a mobile network at the same time, transmits a local host user flag and a service category request flag, connects to a target server, completes a network clock calibration and an electrode pieces adhesion status check. According to a work mode flag, the mobile network terminal device enters into a cardiac electricity and breast impedance data monitor status, the electrophysiological data collection module collects cardiac electricity and breast impedance data synchronously through the cardiac electricity electrodes on the patient's breast, converts an analog signal into a digital signal through an internal A/D analog-digital convertor, sends it to the baseband processor for analyzing and processing through a SPI series communication interface, parses the rhythm and rate data of breath and the rhythm, rate, and modality data of the cardiac electricity, stores it in a cardiac electricity and impedance data storage area in the data storage card. Sleep snore data is recorded by the voice communication module, and stored in a sleep snore data storage area in the data storage card. The mobile network terminal device reads data of left-right, pitching, standing posture in a human posture sensor in the external micro current stimulator module, stores it in a posture data storage area in the data storage card, and reads the data of a blood oxygen saturation sensor, stores it in a blood oxygen saturation data storage area in the data storage card.

The application program module comprehensively analyzes the breath data, the cardiac electricity data, the snore data, the blood oxygen saturation data and the posture data, and compares such data with respective reference value set in the application program module. When the data exceeds the reference value, the application program module identifies that the patient is in a serious sleep apnea or the apnea incurs a disordered cardiac electrophysiology, sets an alert flag, packages the data, and sends it to the target server for further analyzing and processing. If the target server confirms the data belongs to a high-risk status, an intervening instruction is sent to the mobile network terminal device. The mobile network terminal device enables the external micro current stimulator module to release current to stimulate the patient to change posture or be aroused from sleep, open the respiratory tract, recover the breath function, cancel the factors incurring the disordered cardiac electrophysiology. Meanwhile, the data after intervening is packaged and sent to the target server, so as to confirm the intervening effect. In such a way, the disease is prevented from deteriorating, and the patient's life can be saved.

The reference value set in the application program module is set according to a serious adverse impact extent of the apnea status imposed on the patient determined by the doctor in advance. For example, more than 15 seconds of the apnea time, more than 30 per hour of an incidence rate of the apnea event, less than 40 per minute of cardiac rhythm, a non-sustained ventricular tachycardia, an acute myocardial ischemia, and a non-heart-beating, etc. are all likely to endanger the life safety of the patient. The content analyzed comprehensively by the mobile network terminal device at least includes a count and duration of apnea per unit time, a variation count and duration of a modality of the cardiac electricity, a rate and a rhythm, and a variation count and duration of a sleep snore.

A default work mode of the mobile network terminal device is a stand-alone and off-line work status. After the user starts the mobile network terminal device, the application program module comprehensively analyzes the breath data, the cardiac electricity data, the snore data, the blood oxygen saturation data, and the posture data. When the patient is found in a serious sleep apnea or the apnea incurs a disordered cardiac electrophysiology, the mobile network terminal device transmits an alert flag, enables the external micro current stimulator module to release current to stimulate the patient to change posture or be aroused from sleep, opens the respiratory tract, recovers the breath function, cancels the factors incurring the disordered cardiac electrophysiology. Meanwhile, an audio and light alert is trigged to promote the patient and the relatives. After finishing the monitoring, the patient can access the internet and upload the recorded and stored data to the target server so as to obtain advice from the doctor.

According to the work mode flag, the mobile network terminal device may also make independently a electrophysiology data remote monitoring for 24 hours, a image video remote monitoring, a sleep snore remote monitoring, a VoIP voice communication, and a network emergency recourse. The target server may enable the mobile network terminal device by a remote control to send and upload data in accordance with the doctor's instruction, and work in accordance with the instructions of the target server, exchanges data information mutually in bi-directions.

The present invention is characterized in that a hardware architecture of the mobile network terminal device comprises a baseband processor and a configured periphery hardware function module, establishes a data connection with the mobile network and the target server, makes a real-time monitor analysis and network data information exchange, and controls the work status of the micro current stimulator module at the same time. The baseband processor module is responsible for processing the breast impedance data, the electrophysiology data, the sleep snore data, the image and video data, and the human posture data, the blood oxygen saturation data, the body temperature data from the external micro current stimulator module, demonstrates sufficiently the powerful function of the baseband processor with respect to high-speed computing and digital information, graphic and information processing, and network communication, implementing a collection and analysis and a network data information exchange function of a plurality of critical data with a concise hardware structure. The baseband processor module includes at least the operation system, a microprocessor unit (MCU), a digital signal processor unit, a coprocessor unit, a system bus, a periphery bus, a bridge unit, an interface for the periphery bus, a data memory unit, a direct access memory unit, a buffer memory unit, a work power supply management unit, a baseband unit, a frequency control unit, a system clock unit, a real time clock unit, a timer GPT unit, and a periphery instrument and an interface thereof. The periphery instrument and the interface thereof include a keyboard control unit, a graphic and image display control unit, an image/picture collection process unit, an audio process unit, a data storage card control unit, a data memory control unit, an asynchronous series communication port UART unit, a USB controller unit, a JTAG test unit, a USIM card control unit, and a radio frequency unit.

The features of the present invention lie in the microprocessor control unit (MCU) of the baseband processor module controls the operation of each function unit and periphery instrument; the system clock unit provides the system with a task schedule reference; the real time clock unit provides a timer GPT with a clock source; the work power supply management unit provides each function unit and periphery instrument with a work power supply; the GPTn in the timer GPT unit generates a preset interrupt frequency; the buffer memory unit buffers, transits, and stores various data; the USIM card control unit is connected to a client identity recognition USIM card so as to provide the mobile network with identity recognition data of a local host; the baseband unit and the frequency control unit are connected with the radio frequency antenna, so as to control the modulation and demodulation of the signal, and the signal conversion between an external radio frequency signal and a signal of the baseband unit; the SPI series communication interface is connected to the electrophysiological data collection module, so as to receive the breast impedance and cardiac electricity digital signal; the keyboard control unit is connected to the keyboard module, so as to issue various control instructions of the mobile network terminal device, and input and/or set user information data; the graphic and image display control unit is connected to the graphic and image display module, so as to display a human machine interaction interface, a webpage access interface, a selection list, and a text viewing pages; the image/picture collection process unit is connected to the image and picture sensor, so as to collect the image video data of the user; the audio process unit is connected to the voice communication module, so as to enable the VoIP voice communication of the mobile network terminal device, and a process of a voice broadcasting of the doctor's advice, the doctor's leave word, and the sleep snore record; the data storage card control unit is connected to the data storage card, encodes and stores in partition various monitor data and the image and video data of the mobile network terminal device; the data memory control unit is connected to the data memory, so as to store an application program of the mobile network terminal device, including a user information file and a configuration file, user setting information data, two dimensional recognition data, and medical evidence data, etc.; a UART1 in an asynchronous series communication port UART unit is connected to the short distance digital communication module, so as to enable a short distance data/information exchange between the mobile network terminal device, the micro current stimulator module, and the external Wi-Fi device, and a UART2 is connected to the GPS receiver module, so as to enable a satellite positioning of the mobile network terminal device; the USB controller unit is connected to the USB interface module, so as to enable a large volume data/information exchange between the mobile network terminal device and a computer device.

The features of the present invention lie in the electrophysiological data collection module of the mobile network terminal device comprises a plurality of analog signal input terminals, a pre-amplification circuit, a breast impedance detection circuit, a heart pacemaker signal detection circuit, a common mode negative feedback circuit, an A/D analog-to-digital conversion circuit, and a SPI output terminal of the module is connected to a SPI series communication port of the baseband processor, and the baseband processor reads data for analyzing and processing.

The features of the present invention lie in that the data memory of the mobile network terminal device is used to store user information data input by the keyboard module, and the user information data includes, but is not limited to, an access point domain name, a target server fixed IP address, a user name and password, a SMS number, a MMS address, a VoIP access information, a default target address list, a user identity, a dwelling location, a blood type, a society medical guardianship card number, a medical record summary containing a user disease diagnosis, and recourse text information. The user information data is used to a wireless access and a network data/information exchange for a network level, and is used to provide an identity authentication and a brief disease history in the network data exchange, and is also used to establish a VoIP voice communication channel between the mobile network terminal device and the callee at the target end, so as to make voice medical consultation and send a recourse text of "need help" over the mobile network.

The features of the present invention lie in that the data storage card of the mobile network terminal device is encoded so as to be divided into a cardiac electricity and impedance data storage area, a electrophysiological data storage area, a sleep snore data storage area, a image video data storage area, a posture data storage area, a blood oxygen saturation data storage area, a body temperature data storage area, a position information data storage area, a multimedia data storage area under the control of the application program module, and these storage areas are used to store continuous monitoring cardiac electricity and breast impedance data, the sleep snore data, the image video data, the posture data, the blood oxygen saturation data, the body temperature data, the position information data, the multimedia data, and various analysis diagnosis parameter information, statistic information, and time information of the mobile network terminal device. When the mobile network terminal device makes a data/information exchange at the network level, it reads data from the preset area of the data storage card, packetizes the data, and the packetized data further includes the data of the local host user medical record summary, the society medical insurance card number, and the position information.

The present invention is characterized in that an external micro current stimulator module controlled by wireless connection, the micro current stimulator module comprises a main controller MCU, a voltage/current conversion circuit, a micro current stimulation electrode, a body posture sensor, a blood oxygen saturation sensor, a body temperature sensor, a Bluetooth circuit, a memory circuit, a work power supply, and a fixing adhesive tape. Under the control of the mobile network terminal device, the variation of the posture, the blood oxygen, the body temperature is monitored and used as a index parameters for analyzing and diagnosing the sleep apnea, and the current may be controlled to be released by level at the same time, the patient is stimulated to change posture or be aroused from sleep, open the respiratory tract, and recover the breath function.

The present invention provides a cardiac electricity and breath data monitor mobile network terminal device having function of micro current release, comprises an application program module executed in the operation system for controlling the work mode of the mobile network terminal device. The word mode comprises a cardiac electricity and breath data monitor mode, a electrophysiology data monitor mode, a sleep snore data monitor mode, an image and video monitor mode, a short distance data communication monitor mode, a VoIP voice communication mode, and a network emergency recourse mode.

As compared with the prior art, the advantage of the present invention is that:

the defects in the existing home sleep apnea monitor technology are overcame, a large number of various instruments and devices is replaced by a concise hardware structure, implementing a synchronous monitor and real-time analysis of breath and cardiac electricity, and a real-time intervening function, providing the remote doctor with important data, such as breath, cardiac electricity, snore, blood oxygen, and so on, and a result of analyzing and screening. When necessary, a micro current is controlled to be released by level to intervene, so as to stimulate the user to change posture or be aroused from sleep, recover the breath function, cancel the factors incurring the disordered cardiac electrophysiology, resolving effectively the requirement of the doctor and the patient, which may be used as a long-term used medical tool for the large number of the patients suffering from sleep apnea syndrome and has a wide application prospect.

For a further explanation on the principle and characteristic of the present invention, the detailed illustration of the present invention will be made in connection with the drawings and the specific embodiments as follows.

DETAILED DESCRIPTION OF THE PREFERRED EMBODIMENTS

The specific embodiment of the present invention will be described in detail in connection with the drawings in the following.

In accordance with one embodiment of the present invention, the mobile network terminal device of the present invention will be described. However, those skilled in this art should understand that the application of the present invention is not limited to certain standard baseband processor module and certain operation system, and other operation systems including, but is not limited to, Windows mobile, Android, Linux, Palm OS, Symbian, OSE, Nucleus, and so on, may be used with the present invention.

Figure 1:
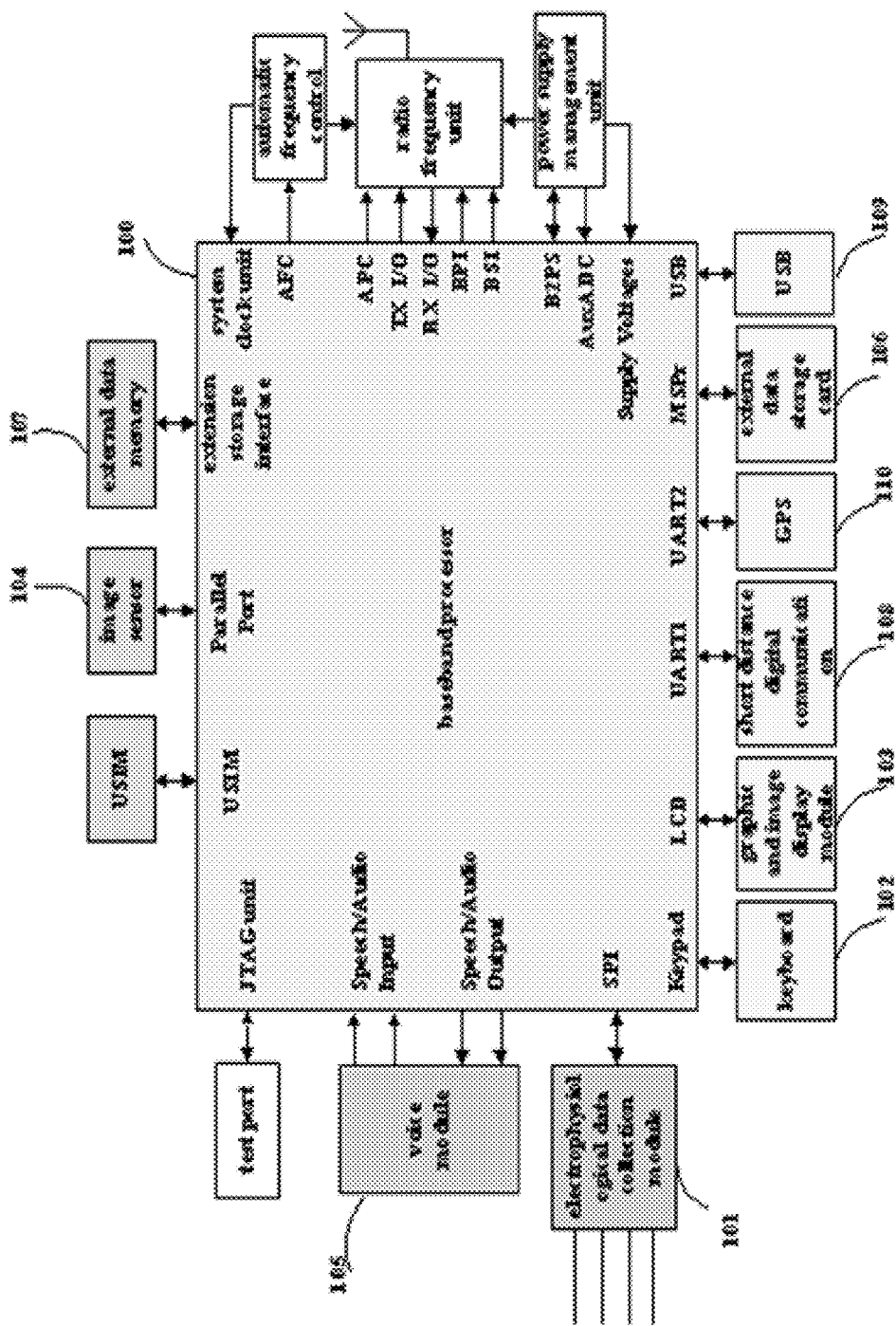
FIG. 1 is a principle block diagram of a cardiac electricity and breath monitoring mobile network terminal device having function of micro current release according to one embodiment of the present invention.

FIG. 1 is a principle block diagram of the cardiac electricity and breath monitoring mobile network terminal device having function of micro current release according to one embodiment of the present invention. The mobile network terminal device includes a baseband processor module 100, an electrophysiological signal collection module 101, a keyboard module 102, a graphic and image display module 103, an image and picture sensor 104, a voice module 105, a data storage card 106, a data memory 107, a short distance digital communication module 108, a USB module 109, a GPS receiver module 110, an application program module 200 set to operate under the operation system in the baseband processor module 100, and an external micro current stimulator module. Meanwhile, the operation system is further embedded with a TCP/IP protocol stack, a WAP browser, a short distance digital communication protocol, a USB protocol, an instant message protocol, a VoIP voice communication protocol, a multimedia software, a general language text font, and the like.

The mobile network terminal device is controlled by the application program module to make a choice to set user information data, a function status, and a work mode; makes a remote monitoring of the cardiac electricity and breath data, a remote monitoring of the electrophysiological data, a remote monitoring of an image and video, a monitoring of a sleep snore, a short distance data/information exchange, a USB large volume data/information exchange, a medical consultation VoIP voice communication, a network emergency recourse, and the like.

The external micro current stimulator module has a function of micro current release, posture monitoring, blood oxygen monitoring, body temperature monitoring, Bluetooth short distance digital communication, and the like, provides the posture data, the blood oxygen saturation data, and the body temperature data during sleep for the mobile network terminal device. Since both of them are connected to each other by Bluetooth, the external micro current stimulator module may be placed on the arms or legs in the body flexibly and work under the wireless control of the mobile network terminal device.

A hardware architecture of the mobile network terminal device comprises a baseband processor and a configured periphery hardware function module, establishes a network connection with the target server through the mobile network or Wi-Fi, makes a real-time monitor analysis and network data information exchange, and controls the work status of the micro current stimulator module at the same time. The target server may enable the mobile network terminal device by a remote control to send data in accordance with the doctor's instruction, and work in accordance with the instructions of the target server, exchanges data information mutually in bi-directions. The baseband processor module is responsible for processing the breast impedance data, the electrophysiology data, the sleep snore data, the image and video data, and the human posture data, the blood oxygen saturation data, the body temperature data from the external micro current stimulator module, demonstrates effectively the powerful function of the baseband processor with respect to high-speed computing and digital information, graphic and information processing, and network communication, implementing a collection and analysis and a network data information exchange, and a real-time intervening function of a plurality of critical data with a concise hardware structure, which may monitor and record a plurality of critical data of the patient during sleep for continuous several days, providing a real-time analysis and screen and a real-time intervening and protecting function which cannot be provided by the existing technology.

FIG. 1 illustrates a relationship between the internal function units of the baseband processor 100 and the peripheral devices according to one embodiment of the present invention. The microprocessor control unit (MCU) of the baseband processor module 100 controls the operation of each function unit and periphery instrument; the system clock unit provides the system with a task schedule reference; the real time clock unit provides a timer GPT with a clock source; the work power supply management unit provides each function unit and periphery instrument with a work power supply; the GPTn in the timer GPT unit generates a preset interrupt frequency; the buffer memory unit buffers, transits, and stores various data; the baseband unit and the frequency control unit are connected with the radio frequency antenna, so as to control the modulation and demodulation of the signal, and the signal conversion between an external radio frequency signal and a signal of the baseband unit; the USIM card control unit is connected to a client identity recognition USIM card 111, so as to provide the mobile network and the remote server with identity recognition data of a local host; the SPI series communication interface is connected to the electrophysiological data collection module 101, so as to receive the cardiac electricity and breast impedance digital signal; the keyboard control unit is connected to the keyboard module 102, so as to input various control instructions of the mobile network terminal device, and input user information data; the graphic and image display control unit is connected to the graphic and image display module 103 for displaying a human machine interaction interface, a selection list, and a medical materials electronic text viewing page in a multimedia work mode, etc.; the image collection process unit is connected to the image sensor 104, so as to collect the image video data of the user; the audio process unit is connected to the voice communication module 105, so as to enable the VoIP voice communication of the mobile network terminal device, and a process of a voice broadcasting of the doctor's advice, the doctor's leave word, and the sleep snore data record; the data storage card control unit is connected to the data storage card 106, encodes and stores in partition various monitor data and the image and video data of the mobile network terminal device; the data memory control unit is connected to the data memory 107, so as to store an application program of the mobile network terminal device, including a user information file and a configuration file, user setting information data, two dimensional recognition data, and medical safety data, etc.; a UART1 in an asynchronous series communication port UART unit is connected to the short distance digital communication module 108, so as to enable a short distance data/information exchange between the mobile network terminal device and an external device, and a UART2 is connected to the GPS receiver module 110, so as to enable a satellite positioning of the mobile network terminal device; the USB controller unit is connected to the USB interface module 109, so as to enable a large volume data/information exchange between the mobile network terminal device and a computer device. According to the work mode selected and set by the mobile network terminal device, the baseband processor module 100 processes the breast impedance data and cardiac electricity data, the image and video data, the sleep snore data, the posture data, the blood oxygen saturation data, and so on, implementing respective functions of the mobile network terminal device.

Figure 2:
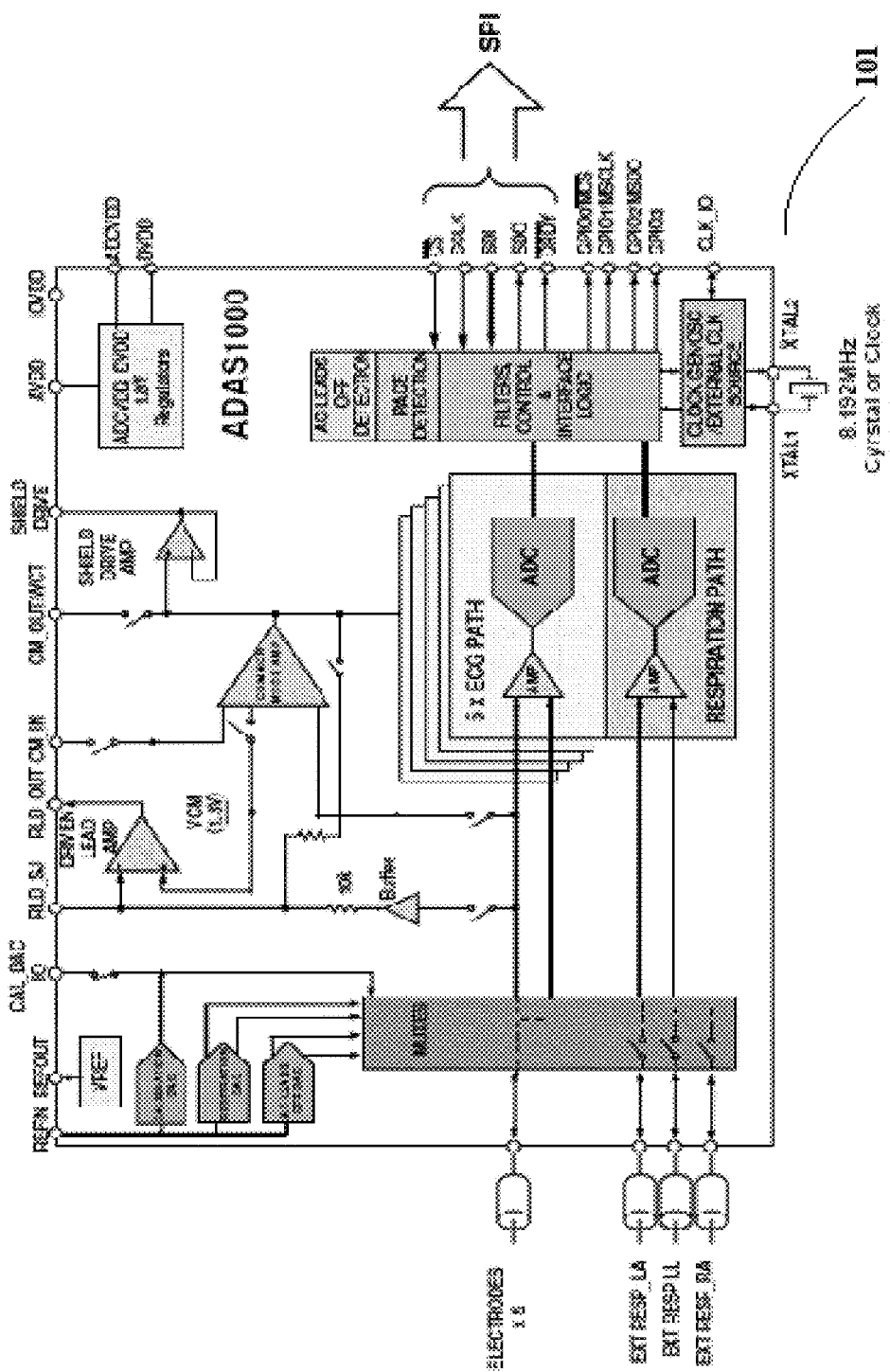
FIG. 2 is a principle block diagram of an electrophysiological data collection module used in one embodiment of the present invention.

FIG. 2 illustrates the electrophysiological data collection module 101 according to one embodiment in the present invention, comprising a plurality of analog signal input terminals, and a pre-amplification circuit, a breast impedance detection circuit, a heart pacemaker signal detection circuit, a common mode negative feedback circuit, an A/D analog-to-digital conversion circuit, and a SPI output terminal of the module is connected to a SPI series communication port of the baseband processor, and collects and transports the breast impedance data and cardiac electricity data to the baseband processor for analyzing and processing. A breath status measurement method of the module is to drive a high frequency 46.5 kHz differential current into two cardiac electricity electrodes on the patient's breast, thus the resulting differential voltage causes by the change in the impedance is changed, and an analog signal of a breath rate, and a rhythm change is obtained to be sent into the internal A/D converter together with the cardiac electricity data for a conversion into a digital signal. Preferably, according to one embodiment of the invention, the electrophysiological signal collection module employs an ADAS1000 analog front-end chip with low power consumption by ADI corp., which may collect the cardiac electricity and the breast impedance data synchronously, and may collect the cardiac electricity data individually.

FIG. 1 illustrates the keyboard module 102 according to one embodiment of the present invention, which employs a touch-control type keyboard, being connected to interface of the keyboard control unit of the baseband processor module 100. Under the control of the application program module 200, various control instructions are input via the keyboard module 102. The instructions include, but are not limited to, a selection and/or setting of the function status, a selection and/or setting of the work mode, and an input and/or setting of the user information data. The set user information data is classified and stored into a user information file and a configuration file of the data memory 107. The user information data includes, but is not limited to, a fixed IP address of a target server, an access point domain name, a user name and password, a SMS number, a MMS address, a VoIP access information, a default target address list, a user identity, a dwelling location, a blood type, a society medical guarantee card number, a medical record summary, and a text information. According to one embodiment of the invention, the keyboard module 102 employs a capacitance and touch type keyboard.

FIG. 1 illustrates that the graphic and image display module 103 in accordance with one embodiment of the present invention is connected to the interface of the graphic and image display control unit of the baseband processor 100. By means of the application program module 200, the mobile network terminal device controls the graphic and image display module 103 to display a human machine interaction interface, a webpage access interface, a function selection list, a work status selection list, data, an image, a graphic, a text, a letter, and various electrophysiological graphics may also be displayed/frozen by scrolling in real time. In the alarm alert status, the graphic and image display module 103 prompts the user by the text and the light on the screen thereof. Preferably, according to one embodiment of the invention, the graphic and image display module 103 employs a color liquid crystal with 480×320 pixels.

FIG. 1 illustrates that the image sensor 104 in accordance with one embodiment of the present invention is connected to the interface of the image collection process control unit of the baseband processor module 100. When the mobile network terminal device enables a cardiac electricity and breast impedance monitoring mode, an image and video monitoring mode may be selected to work synchronously, and the application program module 200 enables the image sensor 104.

According to the set monitor time length and monitor manner, the image or video data of the user may be taken continuously or discontinuously, and the application program module 200 compresses data, and sends it to an area set by the data storage card 106 for storage. When the mobile network terminal device sends the cardiac electricity and breast impedance data, the application program module 200 reads the image or video data in corresponding time period according to a cardiac electricity and breast impedance data flag time, packetizes it to send to the target server.

The mobile network terminal device may enable independently the image and video monitoring mode to work according to the instructions input via the user's keyboard or from the target server, take the image or video data of the user continuously or discontinuously, send the data to the target server for analyzing and processing after the compression and process, and receives a process advice replied by the target server at the same time. Preferably, according to one embodiment of the invention, the image sensor 104 employs a high resolution camcorder with higher than 3,000,000 pixels.

FIG. 1 illustrates the voice module 105 in accordance with one embodiment of the present invention is comprised of a speaker, an earpiece, and a microphone, which are connected to the interface of the audio process unit of the baseband processor module 100, so as to enable network voice communication of the mobile network terminal device. When the mobile network terminal device is set to a VoIP voice communication mode, the VoIP access information and the default target address stored in the external data memory 107 are read by the application program module 200 according to the work mode flag, a call establishing request is launched, the callee responds to this request, and the user makes voice medical consultation or voice communication with the callee at the target end by the voice module 105. The default target address can be set as an address of a target hospital doctor solely, and can also be set to be a plurality of target addresses involving the relatives of the user. Preferably, in accordance with one embodiment of the present invention, the voice module 105 uses a general micro speaker, a general earpiece, and a general microphone.

Under the control of the application program module 200, the voice module 105 can voice report the doctor's advice on diagnosis and process, a doctor's leave word, a medical log content preset by the user, an alarm alert, and an audio play replied by the target server.

When the mobile network terminal device is set to the cardiac electricity and breast impedance monitoring mode, the sleep snore data monitoring mode may be selected to work synchronously. Under the control of the application program module 200, the voice module is enabled, and according to the set record length and record manner, the snore may be recorded continuously or discontinuously, and the record start and end times of the collected snore is tagged, subjected to a compression process, and sent to the sleep snore data storage area of the data storage card 106. When the mobile network terminal device sends the cardiac electricity and breast impedance data, the application program module 200 reads the sleep snore data during the period, and the data is packetized to be sent to the target server.

The mobile network terminal device may enables independently the sleep snore data monitoring mode according to the transmission instruction sent by the user's keyboard or the instructions sent by the target server. Under the control of the application program module 200, the voice module records the snore continuously or discontinuously according to the set record length and record manner, and the collected snore data is tagged with a record start time, and an end time, sent to the sleep snore data storage area for storage after compression and process. When the application program module 200 calculates the snore interval to be greater than 10 seconds, an alarm flag is sent, and the posture data, the blood oxygen saturation data, and the body temperature data in the corresponding time period is read, the data is packetized to be sent to the target server for further processing.

FIG. 1 illustrates that the data storage card 106 in accordance with one embodiment of the present invention is connected to the interface of the data storage card control unit of the baseband processor module 100. The mobile network terminal device controls the data storage card 106 to be encoded, so as to be divided into a cardiac electricity and breast impedance data storage area, a electrophysiological data storage area, a image video data storage area, a sleep snore data storage area, a posture data storage area, a blood oxygen saturation data storage area, a body temperature data storage area, a position information data storage area, a multimedia data storage area under the control of the application program module 200, and these storage areas are used to store continuous monitoring cardiac electricity and breast impedance data, the image video data, the sleep snore data, the posture data, the blood oxygen saturation data, the body temperature data, the position information data, the multimedia data, and various analysis diagnosis parameter information, and statistic information of the mobile network terminal device. Preferably, according to one embodiment of the invention, the data storage card 106 employs a TF card with more than 4G capacity, which may provide a continuous monitoring data for several weeks for a qualitative and quantitative analysis.

FIG. 1 illustrates that the data memory 107 in accordance with one embodiment of the resent invention, which is used to store the application program module 200 (including a user information file and a configuration file), user setting information data, two dimensional code recognition data, and medical evidence data, etc., is connected to the interface of the data memory control unit of the baseband processor module 100. The user setting information data includes, but is not limited to, a target server fixed IP address, an access point domain name, a user name and password, a SMS number, a MMS address, a VoIP access information, a default target address list, a user identity, a dwelling location, a blood type, a society medical guarantee card number, a medical record summary, a text information, and a function setting information data, etc., and the user information data is used to a wireless access and data information exchange of the network level of the mobile network terminal device, and is used to the identity authentication in the data exchange and the provision of the brief medial history. In addition, the user information data is also used to establish a VoIP voice communication channel between the mobile network terminal device and the callee at the target end, so as to enable voice medical consultation. The medical service evidence data is operation information data of the mobile network terminal device, and includes an electrophysiological monitoring mode and date/time, an alarm content and date/time, a sent data content and date/time, a network connection count/status and date/time, received doctor advice and date/time, a content responded to a control command and date/time, an emergency recourse event date/time and response date/time. The medical evidence data is circularly stored, and cannot allowed to be deleted manually by the user. Preferably, in accordance with one embodiment of the present invention, the data memory 107 uses a Flash data memory with a high capacity.

FIG. 1 illustrates that the short distance digital communication module 108 in accordance with one embodiment of the present invention is connected to the UART1 interface in the asynchronous series communication port UART unit of the baseband processor module 100, which is used for a short distance data information exchange of the mobile network terminal device. The short distance digital communication circuit supports Bluetooth and Wi-Fi 802.11x protocols. Bluetooth is used to connect the mobile network terminal device to the external micro current stimulator module wirelessly, and Wi-Fi is used to connect the mobile network terminal device to the external Wi-Fi network device wirelessly, under the control of the application program module 200. Preferably, according to one embodiment of the invention, the short distance digital communication module 108 uses a dual-mode MTK 7650 chip.

The mobile network terminal device enables the Bluetooth of the short distance digital communication module 108 under the control of the application program module 200 to establish a data link with the external micro current stimulator module, read the posture data, the blood oxygen saturation data, and the body temperature data according to the set time, stores them into the corresponding data storage area in the external data storage card 106. If the mobile network terminal device receives a current release instruction from the target server or generates a current release instruction when operating in a stand-alone work mode, it sends immediately an instruction for enabling and releasing a micro current to the micro current stimulator module to stimulate the patient to change the posture or be aroused from sleep, and recover the normal breath.

The mobile network terminal device enables the Wi-Fi of the short distance digital communication module 108 under the control of the application program module 200 to search for the APs of nearby Wi-Fi automatically, read the user name and password set by the patient user, access to the set AP automatically, establish a data link with the target server, send data packet, receive the instructions given by the target server, and process the doctor's advice, providing a second data link connected to the target server for the mobile network terminal device.

FIG. 1 illustrates a USB control unit interface of the USB interface module 109 for connecting to the baseband processor module 100 according to one embodiment of the invention, which is used to connect the mobile network terminal device to the USB interface of the external computer device for a large volume data/information exchange. Preferably, in accordance with one embodiment of the present invention, the USB interface module 109 uses a general micro USB plug.

FIG. 1 illustrates the GPS receiver module 110 in accordance with one embodiment of the present invention is connected to the UART2 interface in the asynchronous series communication port UART unit of the baseband processor module 100, which is used for the satellite positioning of the mobile network terminal device so as to obtain the information on the position where the mobile network terminal device is located. The information on the position includes longitude, latitude, and ellipse height data. The position information is sent to and stored in the position information storage area of the data storage card 106, so as to provide the target server with the information on the position where the user is located while exchanging the network data. Preferably, according to one embodiment of the invention, the GPS receiver module 110 uses a Infineon XPOSYS chip.

Figure 3:
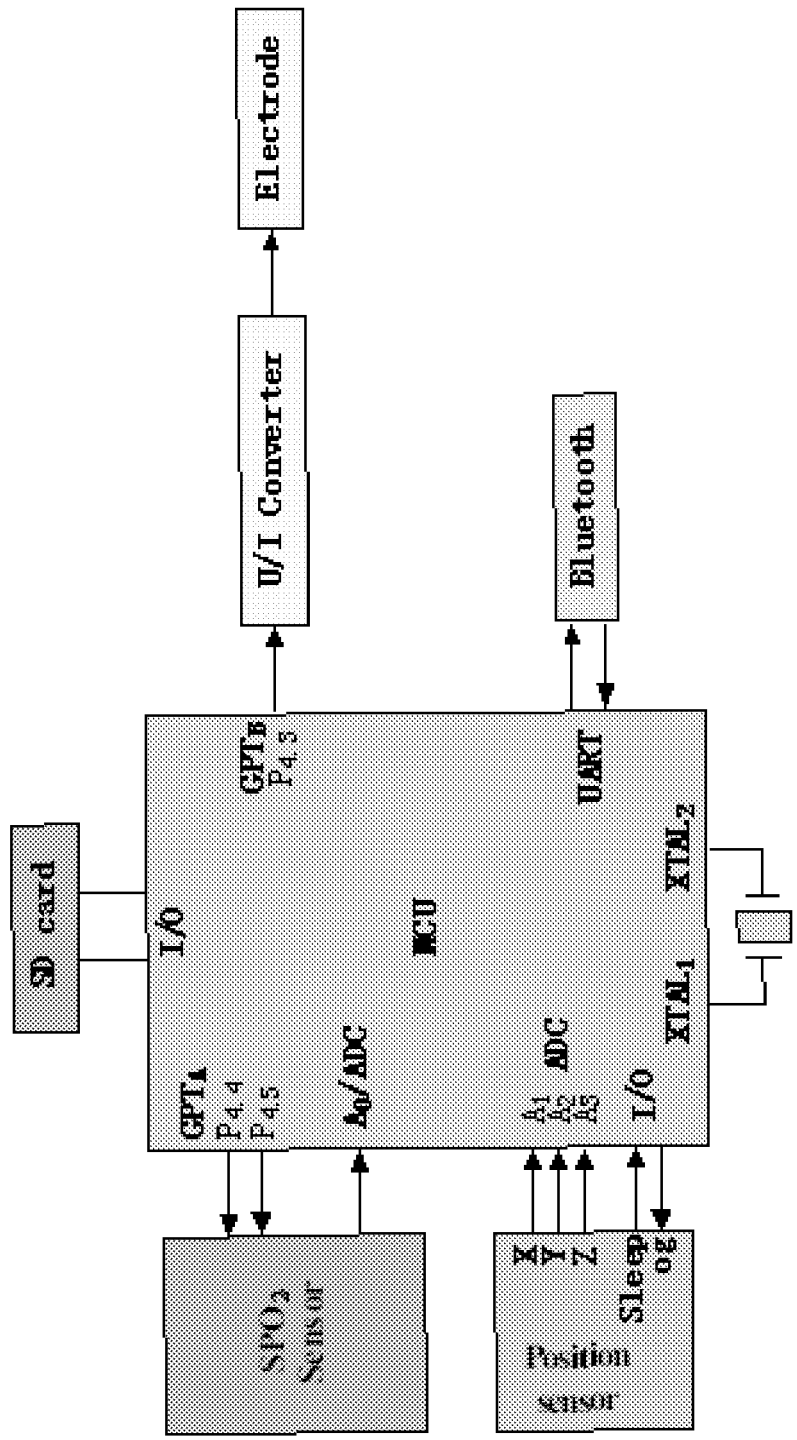
FIG. 3 is a principle block diagram of a micro current stimulator module used in one embodiment of the present invention.

FIG. 3 illustrates the principle block diagram of the external micro current stimulator module according to one embodiment of the invention, including a controller MCU, a Bluetooth circuit, a voltage/current conversion circuit, a current stimulation electrode, a posture sensor circuit, a blood oxygen saturation sensor circuit, a body temperature sensor circuit, a work power supply, and a fixing adhesive tape. The controller MCU uses a MSP 430 MCU with low power consumption, of which the output I/O port of the timer B is connected to the voltage/current conversion circuit. A set digital pulse modulated waveform (PWM) is generated by the timer B under the control of the program, converted into an analog voltage through a low-pass filter for outputting. The voltage is converted into a constant current stimulation signal by the voltage/current conversion circuit, loaded and released into the body by the current stimulation electrode to stimulate the local nerves and muscles to be excited, and the muscle tissues generates a push-pull-like action. The intensity of the released current is 1999 microampere at most. The frequency range of the released current is between 5 Hz to 10 KHz. The current is released by level under the control of the mobile network terminal device, such that the objective of stimulating the patient to change posture or be aroused from sleep so as to recover the breath function can be achieved. This is safe and reliable. The size of the micro current stimulator module is small, and may be placed on a position of the skin of the belly, arms, legs, and so on by the fixing adhesive tape.

An analog/digital (A/D) multi-convertor built in the MSP 430 MCU are connected to the X, Y, and Z output ends of the posture sensor circuit and the output ends of the blood oxygen saturation sensor circuit and the body temperature sensor circuit. An output I/O port of a timer A is connected to a driving end of the blood oxygen saturation sensor circuit to provide it with two driving currents. Under the control of the program, the built-in analog/digital (A/D) multi-convertor collects and converts the analog signal of the body posture, the blood oxygen saturation and the body temperature into the digital signal, and sends them to the memory circuit for storage by category. Both of the blood oxygen saturation sensor circuit and the body temperature sensor circuit use the general standard circuits, and the principle thereof is omitted.

The micro current stimulator module is capable of wirelessly connecting via Bluetooth thereof to a handheld device in which the application program is installed, accepting the control of the handheld device, and operating according to an instruction of the handheld device. The handheld device at least includes a digital mobile phone, a laptop computer and a tablet computer.

Figure 4:
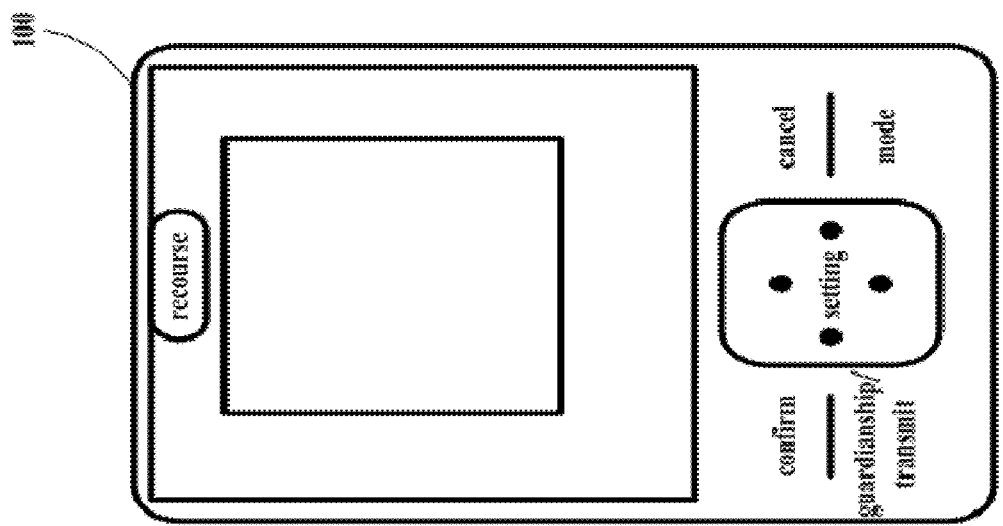
FIG. 4 is a schematic diagram of a control of a wireless connection between the mobile terminal device and the micro current stimulator module in one embodiment of the present invention.
Figure 4:
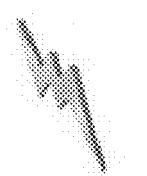
Figure 4:
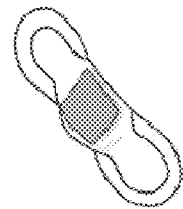

FIG. 4 illustrates a work schematic diagram in which the mobile network terminal device is wirelessly connected to the external micro current stimulator module for a control according to one embodiment of the invention. When the micro current stimulator module starts and works, the MSP 430 MCU controls the Bluetooth circuit to establish a wireless connection with the mobile network terminal device, calibrates and selects the real-time clock to be the work time reference, controls the voltage/current conversion circuit to be in a sleep status, controls the posture sensor circuit, the blood oxygen saturation sensor circuit, and the body temperature sensor circuit to collect the relevant data according to the set time, and store them into the memory circuit by category. The mobile network terminal device accesses and stores the posture data, the blood oxygen saturation data and the body temperature data into the storage area set in the data storage card 106. The target server analyzes the abnormal data screened by the mobile network terminal device. If it is confirmed that the user is in a serious sleep apnea or the apnea incurs the variation of the heart rhythm, rate, and the ST modality, an intervening instruction will be sent immediately to the mobile network terminal device. The mobile network terminal device sends a current release instruction to the micro current stimulator module, and controls the micro current stimulator module to release a micro current through the electrode attached to the body skin, in order to stimulate the patient to change the posture or be aroused from sleep.

In accordance with one embodiment of the present invention, the power supply management unit of the baseband processor module 100 provides each function unit and periphery instrument with the power supply of +3.3V, −3.3V, +2.8V, +1.8V, +1.2V respectively. In accordance with one embodiment of the present invention, a 3G baseband processor module is used preferably, and other standard baseband processor modules may also be used.

In accordance with one embodiment of the present invention, the general Android embedded operation system is used. In addition, the embedded operation system such as Linux, Window CE, mobile, Palm OS, Symbian, OSE, Nucleus, etc., and the updated version thereof can also be used.

According to one embodiment of the invention, the mobile network terminal device uses a general rechargeable lithium battery with 1200 mAh as the work power supply, and the external micro current stimulator uses a small-sized and high-energy battery with 150 mAh as the work power supply, of which the continuous usage time is more than 72 hours. The two parts are encapsulated into two small-sized housings respectively, and the micro current stimulation electrodes and the electrodes of the blood oxygen saturation sensor and the body temperature sensor are set at the two ends of the bottom of the housing of the external micro current stimulator, and fixed to the body by using the adhesive tape to contact with the surface skin closely. The invention has the advantages of small size, reliable performance, and convenient operation, which has good compatibility.

According to one embodiment of the invention, an emergency call recourse key is set on the housing of the mobile network terminal device. When it is trigged by the patient, a network emergency recourse mode is entered immediately, and the application program module 200 resets the alarm flag, reads the present data in the position information storage area of the data storage card 106, controls the mobile network terminal device to send an audio and a vibration alarm, and sends the local host user flag, the information of "I need help", and the present position information to the target server and the mobile phones of the patient's relatives at the same time.

Figure 5:
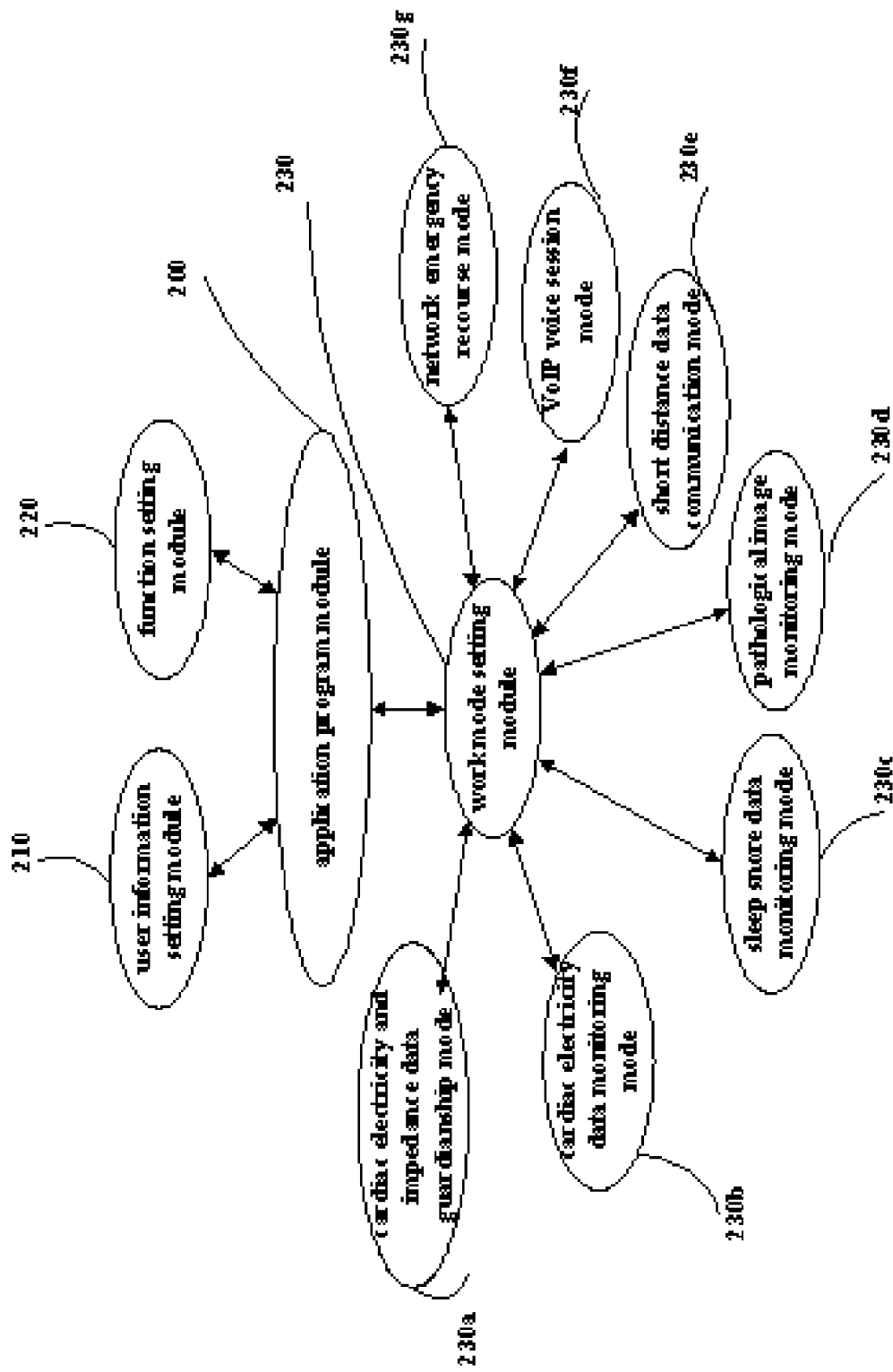
FIG. 5 is a structural diagram of a control of an application program module executed by the mobile network terminal device according to one embodiment of the present invention.

FIG. 5 illustrates a structure of the application program module 200 for controlling the operation of the mobile network terminal device according to one embodiment of the present invention, which comprises:

a user information/data setting module 210, which is responsible for controlling the mobile network terminal device to set and install a domain name, an address, a password, and a user name, a VoIP access information, and a default target address list required by a wireless access on the network level, and a medical record summary, a blood type, and a society medical insurance card, etc., number required by the remote monitoring service;

a function setting module 220, which is responsible for controlling the function setting of the mobile network terminal device, including a selection of the text category, a selection of a voice report, turning on and off of an audio alert, a setting of a high or low volume, a setting of the screen color and luminance of the image and graphic display module, a setting of the multimedia function status, a clearance of the data, and so on;

a work setting module 230, which is responsible for the setting of the work mode of the mobile network terminal device, the work mode comprising a cardiac electricity and breast impedance data monitor mode, a electrophysiology data monitor mode, an image and video monitor mode, a sleep snore data monitor mode, a short distance data communication mode, a USB data communication mode, a VoIP voice communication mode, and a network emergency recourse mode. Wherein, the sleep snore data monitoring is enabled automatically and synchronously when the cardiac electricity and breath data monitor mode is set.

The work mode of the mobile network terminal device may be set independently to the cardiac electricity data monitor work mode, the sleep snore data monitor work mode, and the image and video monitor work mode for a 24-hour multi-lead, such that the doctor and the patient select to set and use depending on the situation.

The work mode of the mobile network terminal device may be set to the short distance digital communication mode, and the mobile network terminal device may go on keeping the digital information exchange with the target server to obtain the service support through the Wi-Fi connected to the target server where the mobile network is interrupted.

In accordance with one embodiment of the present invention, the operation system of the baseband processor module 100 is embedded with a WAP browser and a multimedia software, by which the user may log into the websites and view the web pages. When the function selection is set to the multimedia function status, the graphic and image display module 103 displays the multimedia function list including video, e-book, IQ game, navigation, and the like on the screen. When the user selects the e-book, the e-books, such as medical material, the medicine manual, and so on, may be opened and reviewed; when the IQ game is selected, an IQ recovery game may be played by operating the keyboard; when the video is selected, the video and movie may be received and played, or the movie and TV program stored internally may be played. When the navigation is selected, a GPS position navigation and positioning may be conducted for an easy usage of the patient.

The present invention employs an object-oriented programming language (preferably, C++ language) to write the application program, which has a good extensibility and transplantability, and is suitable for the usage of various standard baseband processors.

Although the specific embodiments of the present invention have been described above, those skilled in this art will understand those specific embodiments are only illustrative explanations. Without departing from the principle and the essential of the present invention, various omissions, replacements and modifications can be made to the details of the above method and device by those skilled in this art. For example, it falls into the scope of the present invention that some steps of the above method are combined, such that substantially same functions are performed in accordance with the substantially same method, so as to achieve substantially same results. Therefore, the scope of the present invention is merely defined by the claims.

What is claimed is:
1. A mobile network terminal device for monitoring cardiac electricity and breath and having a function of micro current release, characterized in that, the device comprises:
    a baseband processor module in which an operation system and an application program module which operates in the operation system are embedded, the baseband processor module is used for processing respective monitoring data of the mobile network terminal device and making a network data/information exchange;

an electrophysiological data collection module for collecting synchronously and converting an analog signal data of the cardiac electricity and breast impedance into a digital signal;

a keyboard module for inputting respective control instructions by a user;

a graphic and image display module for displaying a human machine interaction interface of the mobile network terminal device and a network access webpage;

an image and picture sensor module for obtaining a user image and picture and a video data;

a voice communication module for a VoIP voice communication and a sleep snore data collection of the mobile network terminal device;

a data storage card for storing respective monitoring data, an image and video data, a position information data, and a multimedia data of the mobile network terminal device;

a data memory for storing an application program module of the mobile network terminal device, a user information file, a configuration file, a user setting information data, a two dimensional code recognition data, and a medical service evidence data;

a short distance digital communication module for establishing a short distance data/information exchange channel between the mobile network terminal device and an external apparatus;

a USB interface module for connecting the mobile network terminal device to the external device so as to make a large volume data/information exchange;

a GPS receiver module for a satellite positioning of the mobile network terminal device;

an external micro current stimulator module for collecting posture data, blood oxygen saturation data, body temperature data, and generating and releasing a micro current;

the mobile network terminal device selects and sets a work mode, accesses the network, sends a local host user flag and service flag, establishes a connection with a target server, completes a calibration and tag of the network time, enters into the work mode, collects data for a real-time analysis and process, and accepts and executes an instruction given by the target server under the control of the application program module;

the data collected by the mobile network terminal device is compared with a reference value set in the application program module; when the collected data exceeds the reference value, an alarm flag is set, this abnormal data is uploaded to the target server at the same time;

the reference value set in the application program module is set according to a serious adverse impact extent of the apnea status and heart abnormalities imposed on the patient determined by the doctor in advance.

2. The mobile network terminal device according to claim 1, characterized in that, the electrophysiological data collection module comprises a plurality of analog signal input terminals, in which a pre-amplification circuit, a breast impedance detection circuit, a heart pacemaker signal detection circuit, a common mode negative feedback circuit, an A/D analog-to-digital conversion circuit are included, and a SPI output terminal is connected to a SPI series communication port of the baseband processor, and collects synchronously and transports a plurality of the breast impedance data and cardiac electricity data to the baseband processor for analyzing and processing, a rhythm and rate of a breath wave group and a rhythm, rate and wave group modality of a cardiac electricity wave group are parsed, and the electrophysiological data collection module is a general electrophysiological analog front-end chip.

3. The mobile network terminal device according to claim 1, characterized in that, the external micro current stimulator module comprises a microprocessor control unit (MCU), a voltage/current conversion circuit, a stimulation electrode, a posture sensor circuit, a blood oxygen saturation sensor circuit, a body temperature sensor circuit, a data memory circuit, a Bluetooth circuit, a work power supply, and a fixing adhesive tape; collects and stores posture status data, blood oxygen saturation data, body temperature data; generates and releases a micro current to stimulate a patient for a posture change or an arousal so as to recover the breath function; wherein the released micro current is a constant current, of which the frequency range is between 5 Hz to 10 KHz, and the intensity of the released current is 1999 microampere at most.

4. The mobile network terminal device according to claim 1, characterized in that, the operation system in the mobile network terminal device has at least a TCP/IP protocol, a short distance data communication protocol, a USB protocol, a WAP browser, an instant communication protocol, a VoIP protocol, a multimedia software, and a universal language text font embedded therein, and the operation system is one of the universal embedded operation systems.

5. The mobile network terminal device according to claim 1, characterized in that, the keyboard module is connected to a keyboard control unit interface of the baseband processor module, such that a user control instruction, a human machine interaction operation instruction and user information data are inputted into the mobile network terminal device to select and set a function status and the work mode, wherein the keyboard module being one of the universal touch type keyboards.

6. The mobile network terminal device according to claim 5, characterized in that, the user information data input by the keyboard module comprises an access point domain name, a target server fixed IP address, a short distance data communication key, a user name and password, a SMS number, a MMS address, VoIP access information, a default target address list, a user identity, a dwelling place, a blood type, a society medical guarantee card number, a medical record summary, text information, and the user information file and the configuration file stored in the external data memory by category.

7. The mobile network terminal device according to claim 1, characterized in that, the graphic and image display module is connected to a graphic and image display control unit interface of the baseband processor module, so as to display the human machine interaction interface of the mobile network terminal device, a webpage access interface, a graphic measurement tool interface, a cardiac electricity and breath waveform viewing interface, a function selection and work mode selection list, data, and a text, and the graphic and image display module is a general liquid crystal display with high resolution.

8. The mobile network terminal device according to claim 1, characterized in that, the picture and image sensor is connected to a graphic and image collection and process unit interface of the baseband processor module, such that the mobile network terminal device takes and obtains an image and video data of the user, and the picture and image sensor is a general camcorder module having an auto-zooming function with high resolution.

9. The mobile network terminal device according to claim 1, characterized in that, a transmitter, a receiver and a microphone input terminal of the voice communication module are respectively connected to an audio processing unit interfaces of the baseband processor module, such that the mobile network terminal device records a sleep snore data, makes a VoIP voice communication, voice-broadcasts words left by a doctor, a user-preset medical log content, an audio alarm promotion, and doctor's diagnosis and process advice replied by the target server, wherein the voice communication module is a general transmitter, receiver, and microphone of a handheld device.

10. The mobile network terminal device according to claim 1, characterized in that, the data storage card is connected to a data storage card control unit interface of the baseband processor module, so as to be encoded and divided into a cardiac electricity and breath data storage area, an electrophysiological data storage area, a image video data storage area, a snore data storage area, a blood oxygen saturation data storage area, a body temperature data storage area, a position information data storage area, a multimedia data storage area, and store various data of the mobile network terminal device by category; and the data storage card is a general TF card.

11. The mobile network terminal device according to claim 1, characterized in that, the data memory is connected to a data memory control unit interface of the baseband processor module, such that the mobile network terminal device stores the application program module, the user information file, the configuration file, the user information data, the two dimensional code recognition data, and the medical service evidence data; and the data memory is a general NOR Flash memory.

12. The mobile network terminal device according to claim 1, characterized in that, the short distance data communication module is connected to a UART1 interface in an asynchronous series communication port UART unit of the baseband processor module, supports the 802.11x protocol and the Bluetooth protocol, such that the mobile network terminal device exchanges data and information with an external Bluetooth device and a Wi-Fi device; and the short distance data communication module is a general dual-modes standard short distance communication chip.

13. The mobile network terminal device according to claim 1, characterized in that, the USB interface module is connected to a USB controller unit interface of the baseband processor module, such that the mobile network terminal device is connected with an USB interface of an external computer device to make a large volume data/information exchange.

14. The mobile network terminal device according to claim 1, characterized in that, the GPS receiver module is connected to a UART2 interface in the asynchronous series communication port UART unit of the baseband processor module, such that the mobile network terminal device makes a satellite positioning to obtain information on the position where the user locates, sends the user position information to and stores it in a preset area of the external data storage card, and provides a target server with the user position information while exchanging data and information over the network.

15. The mobile network terminal device according to claim 1, characterized in that, the baseband processor module of the mobile network terminal device is one of the universal baseband processors.

16. The mobile network terminal device according to claim 1, characterized in that, the work mode of the mobile network terminal device includes a cardiac electricity and breath data monitoring mode, an electrophysiological data monitoring mode, an image and video monitoring mode, a sleep snore data monitoring mode, a short distance data communication mode, a USB data communication mode, a VoIP voice communication mode, a network emergency recourse mode and a default work mode, which can be selected and set.

17. The mobile network terminal device according to claim 1, characterized in that, in a default work mode, the mobile network terminal device operates as a stand-alone device in an off-line status to carry out the monitoring and make an analysis; after finishing the monitoring, the user can access the internet and upload the recorded and stored data to the target server so as to obtain advice from the doctor.

18. The mobile network terminal device according to claim 1, characterized in that, the micro current stimulator module is capable of wirelessly connecting via Bluetooth thereof to a handheld device in which the application program is installed, accepting the control of the handheld device, and operating according to an instruction of the handheld device; wherein the handheld device at least includes a digital mobile phone, a laptop computer and a tablet computer.

19. The mobile network terminal device according to claim 1, characterized in that, the micro current stimulator module is encapsulated into a small-sized housing, one or more stimulation electrodes are arranged on the two ends of the bottom of the housing, a blood oxygen saturation sensor electrode and a body temperature sensor electrode are arranged in the middle part of the bottom of the housing, and the bottom of the housing is used to contact with a body skin closely.

* * * * *